United States Patent [19]

Richardson

[11] Patent Number: 4,554,165
[45] Date of Patent: Nov. 19, 1985

[54] METHOD OF MAKING CHEESE WITH PROTEINASE NEGATIVE LACTIC BACTERIA

[75] Inventor: Gary H. Richardson, Logan, Utah

[73] Assignee: Utah State University Foundation, Logan, Utah

[21] Appl. No.: 400,653

[22] Filed: Jul. 22, 1982

[51] Int. Cl.$^4$ .......................... A23C 19/02; C12N 1/20
[52] U.S. Cl. ......................................... 426/36; 426/40; 426/41; 426/43; 435/253
[58] Field of Search ....................... 426/34, 36, 39, 40, 426/41, 42, 43, 61; 435/253

[56] References Cited

U.S. PATENT DOCUMENTS

| | | | |
|---|---|---|---|
| 2,904,437 | 9/1959 | Czarnetzky | 99/9 |
| 3,041,248 | 6/1962 | Hargrove | 195/48 |
| 3,354,049 | 11/1967 | Christensen | 426/39 X |
| 3,420,742 | 1/1969 | Farr | 195/59 |
| 4,191,782 | 3/1980 | Vedamuthu | 426/61 X |
| 4,282,255 | 8/1981 | Gandine et al. | 426/43 X |
| 4,397,926 | 8/1983 | Galal et al. | 426/582 |
| 4,397,927 | 8/1983 | Brog | 426/583 |
| 4,402,986 | 9/1983 | Sinkoff et al. | 426/41 |

OTHER PUBLICATIONS

Mills, et al., Bitterness Development in Cheddar Cheese; Effect of the Level of Starter Proteinase, New Zealand J. of Dai. Sci., and Technol., vol. 15, 1980, (pp. 131-141).
Thomas, et al., Proteolytic Enzymes of Starter Bacteria, Neth. Milk Dairy J. vol. 35, 1981, (pp. 255 & 266-273).
Lawrence, et al., Reviews of the Progress of Dairy Science: Cheese Starters, J. of Dai. Res. vol. 43, 1976, (pp. 141 & 159-161).
Kosikowski, F., Cheese and Fermented Milk Foods, published by the Author, Ithaca, N.Y., 1966, (p. 15).
Kempler, et al., Use of Genetic Alterations to Improve Streptococcus Lactis, 62 as a Potential Cheddar Cheese Starter, J. Dai. Sci., Supplement 1, vol. 62, 1979, (pp. 42-43).
Davies, et al., Reviews of the Progress of Dairy Science; Genetics of Lactic Acid Bacteria, J. of Dai. Res., vol. 48, 1981, (pp. 363-376).
Lowrie, et al., Cheddar Cheese Flavour, IV, A New Hypothesis to Account for the Development of Bitterness, New Zealand, J. of Dai. Sci. and Technol. vol. 7, 1972, (pp. 51-53).
Limsowtin et al., "Agar Medium for the Differentiation of Fast and Slow Coagulating Cells in Lactic Streptococcal Cultures," New Zealand Journal of Dairy Science and Technology, vol. 11, pp. 65-66, (1976).
Mills et al., "Nitrogen Sources for Growth of Lactic Streptococci in Milk," 16, New Zealand Journal of Dairy Science and Technology, 43-55, (1981).
Limsowtin et al., "A new Approach to the Preparation of Bulk Starter in Commercial Cheese Plants," 15, New Zealand Journal of Dairy Science and Technology, 219-224, (1980).

(List continued on next page.)

Primary Examiner—David M. Naff
Attorney, Agent, or Firm—Workman, Nydegger & Jensen

[57] ABSTRACT

Methods and media for preparing bulk cultures of exclusively proteinase negative lactic bacteria and methods for making fermented dairy products such as cheese, cottage cheese, and sour cream employing exclusively proteinase negative lactic bacteria are disclosed. In one preferred embodiment, the medium comprises a whey-based, pH-controlled medium containing sufficient nitrogenous nutrients to render the medium suitable for growing proteinase negative lactic bacteria. The medium is heated to inactivate bacteriophage present therein and subsequently cooled to a temperature favorable to the growth of proteinase negative lactic bacteria, and the proteinase negative lactic bacteria are introduced into the medium and allowed to propagate to a population sufficient to serve as an inoculant in making the particular fermented dairy product. The proteinase negative lactic bacteria culture and an appropriate enzyme are introduced into a vessel containing a quantity of milk where coagulation and syneresis of the milk occurs to produce the fermented dairy product.

35 Claims, 2 Drawing Figures

OTHER PUBLICATIONS

Richardson et al., "USU Lactic Culture System," Utah Science, 94–99, (Winter, 1979).

Lawrence et al., "The Fermentation of Milk by Lactic Acid Bacteria," 29, Society for General Microbiology Symposium 187–219, (1979).

Mills et al., "Release of Cell Wall-Associated Proteinase(s) from Lactic Streptococci," 13, New Zealand Journal of Dairy Science and Technology, 209–215, (1978).

Exterkate, F. A., "Comparison of Strains of *Streptococcus Cremoris* or Proteolytic Activities Associated with the Cell Wall," 30, Neth. Milk Dairy, J. 95–105, (1976).

Law et al., "The Contribution of Starter Streptococci to Flavour Development in Cheddar Cheese," 43, Journal of Dairy Research 301–311, (1976).

Kanasaki et al., "Effect of Temperature on the Growth and Acid Production of Lactic Acid Bacteria—A Rapid Method for the Estimation of Bacterial Populations in Milk," The Australian Journal of Dairy Technology 142–144, (Dec. 1975).

Hillier et al., "Effect of Temperature on the Growth and Acid Production of Lactic Acid Bacteria—The Influence of Added Growth Supplement," The Australian Journal of Dairy Technology, 149–152, (Dec. 1975).

Turner et al., "Uncoupling of Growth and Acid Production in Lactic Streptococci," 10, New Zealand Journal of Dairy Science and Technology, 162–167, (1975).

Martley, F. G. "The Behaviour and Role of Starter Streptococci in Camembert Cheesemaking," 10, New Zealand Journal of Dairy Science and Technology, 12–17, (1975).

Thomas et al., "Starters and Bacteriophages in Lactic Acid Casein Manufacture—Mixed Strain Starters," 38, J. Milk Food Technol., 269–274, No. 5, (May 1975).

Thomas et al., "Starters and Bacteriophages in Lactic Acid Casein Manufacture—Development of a Controlled starter System," 38, J. Milk Food Technol., 275–278, No. 5, (May 1975).

Smith et al., "The Nature of the Stimulation of the Growth of *Streptococcus Lactis* by Yeast Extract," 42, Journal of Dairy Research, 123–138, (1975).

Martley et al., "Cheddar Cheese Flavour—Characteristics of Single Strain Starters Associated with Good or Poor Flavour Development," 7, New Zealand Journal of Dairy Science and Technology, 38–44, (1972).

Lowrie et al., "Cheddar Cheese Flavour—The Growth of Lactic Streptococci During Cheesemaking and the Effect on Bitterness Development," 7, New Zealand Journal of Dairy Science and Technology, 44–50, (1972).

Lawrence et al., "Cheese Starters Under Control," 37, Dairy Industries, 73–78, No. 2, (Feb. 1972).

Webb et al., "Byproducts from Milk," The Avi Publ. Co., Inc., Westport, Conn., 2nd Ed., pp. 43–46, SF 275, A1 W4, (1970).

Hargrove et al., "Phosphate Heat Treatment of Milk to Prevent Bacteriophage Proliferation in Lactic Cultures," 44, J. Dairy Sci. 1799–1810, (1961).

Garvie, E. I., "Some Observations on Slow and Fast Acid-Producing Variants of Strains of *Streptococcus Cremoris* and *Str. Lactis* used as Cheese Starters," 26, J. Dairy Res. 227–237, (1959).

METHOD OF MAKING CHEESE WITH PROTEINASE NEGATIVE LACTIC BACTERIA

BACKGROUND

1. Field of the Invention

The present invention relates to novel methods and media for preparing bulk cultures to be used as inoculants in making fermented dairy products and further relates to novel methods for making fermented dairy products. In particular, the present invention relates to methods and media for preparing bulk cultures of proteinase negative lactic bacteria and to methods for making fermented dairy products, such as Cheddar and other cheeses, cottage cheese, cream cheese, buttermilk, and sour cream, employing such proteinase negative lactic bacteria.

2. The Prior Art

Although the present invention relates to methods for making many different kinds of fermented dairy products, the following discussion of the present invention, as well as the prior art, is generally in terms of cheesemaking. However, since the processes for making other fermented dairy products are closely akin to the processes for cheesemaking, it will be readily understood that the description of the present invention also pertains to the processes for making the other fermented dairy products, unless otherwise indicated.

Cheese is made by the controlled coagulation and syneresis of milk. Each year, the cheesemaking industry in the United States consumes literally billions of gallons of milk for the production of cheese. Coagulation and syneresis of the milk is accomplished by an extract containing an enzyme known as rennin or chymosin, which enzyme is extracted from the fourth or true stomach of a calf. (Other suitable enzyme-containing extracts obtained from bovine, swine, and fungal sources are also sometimes used.)

Upon action by the rennin, the milk is converted into a cheese curd and whey. The activity of the rennin is enhanced or catalyzed by both heat and lactic acid. Generally, lactic acid is supplied by lactic acid-producing bacteria, such as *Streptococcus lactis* and *Streptococcus cremoris*. Such bacteria feed primarily on the lactose in milk to produce the acid needed in the manufacture of cheese.

The development of acid is critical to the success of the entire cheesemaking process. Failure to develop acid properly can result in a soft, high moisture and high pH curd, and can further result in the development of gas, as well as fruity, fermented, or other undesirable flavors. Too much acid can result in a curd which is discolored or which has acidic or bitter flavors, body defects, or a relatively low moisture content. Hence, the proper production of acid through the development of a proper lactic bacteria culture is critical to the successful manufacture of cheese.

A bulk culture of lactic acid-producing bacteria is typically prepared in a vessel known as a bulk culture tank and serves as an inoculant for the milk to be made into cheese. This bulk culture of lactic bacteria generally comprises from between about 0.1% to 7% or more of the total volume of milk to be inoculated. Once a satisfactory lactic bacteria bulk culture has been prepared in the bulk culture tank, the bulk culture is introduced into a cheesemaking vessel containing the milk. The rennin enzyme is also added to the milk in the cheesemaking vessel, and the lactic bacteria cultures propagate while producing the necessary acid to aid the enzyme in producing cheese.

Most lactic acid-producing bacteria (such as *Streptococcus lactis* and *Streptococcus cremoris*) can exist in at least two different forms or phenotypes: proteinase positive (hereinafter sometimes referred to as "Prt+") and proteinase negative (hereinafter sometimes referred to as "Prt−"). The Prt+ lactic bacteria are characterized by an external, cell wall associated, proteinase enzyme system which breaks down casein (and perhaps other proteins) in the milk to simple peptides which are in part consumed during the propagation of the Prt+ lactic bacteria and which can create bitter flavors in the cheese. The Prt− lactic bacteria, on the other hand, are characterized by the absence of such an external, cell wall associated, proteinase enzyme system.

The propagation of Prt+ lactic bacteria has been found to be plasmid-linked, and upon loss of the proteinase-expressing plasmid, the Prt+ lactic bacteria produce Prt− daughter cells. Generally, variant proteinase negative lactic bacteria are produced from the proteinase positive lactic bacteria 1-2% of the time. It should be noted, however, that once the Prt+ lactic bacteria have lost the proteinase-expressing plasmid to produce Prt− lactic bacteria, the Prt− lactic bacteria are subsequently incapable of producing Prt+ lactic bacteria. Thus, introduction of a Prt− lactic bacteria phenotype into a cheesemaking system will result in the propagation of both Prt+ and Prt− lactic bacteria phenotypes; however, the introduction of a Prt− lactic bacteria phenotype into a cheesemaking system will result in the propagation of only the Prt− lactic bacteria phenotype.

In choosing a suitable bacterial strain for use in making cheese, the traditional rule has been that those bacterial strains which are unable to coagulate milk at room temperature in an eighteen to twenty-four hour period are unsuitable. Since, under normal conditions, Prt− lactic bacteria cannot coagulate milk within the traditional twenty-four hour period, the exclusive use of Prt− lactic bacteria for the making of cheese has been completely avoided in the prior art processes. Indeed, the prior art processes have taught away from the use of Prt− lactic bacteria in making cheese and have sought to suppress the production of Prt− lactic bacteria so as to maintain an active culture of Prt+ lactic bacteria.

Thus, while the prior art has recognized that some Prt− lactic bacteria may be employed, the prior art processes have generally sought to minimize the amount of Prt− lactic bacteria used. From the foregoing, it will be appreciated that the prior art processes are concerned mainly with methods for preparing lactic bacteria bulk cultures and for making cheese employing solely or primarily Prt+ lactic bacteria.

Although proteinase positive lactic bacteria have been preferred in the prior art cheesemaking processes, significant problems are inherent in the preparation and use of such Prt+ lactic bacteria cultures. For example, as mentioned above, the proteinase system of Prt+ lactic bacteria has been linked to the occurrence of bitter flavors in the resulting cheese. As the proteinase system breaks down casein in the milk, the resultant simple peptides cause a bitter flavor. Similarly, the proteinase system of the Prt+ lactic bacteria breaks down a considerable amount of casein in the milk which is consumed in the propagation of the Prt+ lactic bacteria, thereby significantly reducing the content of casein in the resultant cheese. The protein content of the resultant cheese is further reduced by the fact that the broken down or solubilized casein not consumed by the growing lactic bacteria is lost in the whey exuded from the curd. Thus, because of the reduction in protein content, the nutritional value of the cheese is correspondingly reduced.

Additionally, as mentioned above, introduction of a pure Prt+ lactic bacteria phenotype into a cheesemaking operation soon results in a mixture of both Prt+ and Prt− lactic bacteria phenotypes, thus introducing complex variables into the strategy of strain selection and propagation. Since the exact ratio of Prt+ to Prt− lactic bacteria will vary with time, it is difficult to control the production of Prt+ lactic bacteria. The result is that it is difficult to control the production of acid and thus to predict just how long it will take to produce the cheese.

Moreover, the ratio of Prt+ to Prt− lactic bacteria in the Prt+/Prt− lactic bacteria blend of the prior art processes may ultimately decrease to the point that the blend becomes incapable of producing lactic acid at a rate fast enough to carry out the cheesemaking process. This is due to the fact that in the prior art processes where Prt+/Prt− lactic bacteria blends occur, the growth of the Prt− lactic bacteria depends on the ability of the Prt+ lactic bacteria to break down casein and thereby produce sufficient nitorgenous nutrients for such growth. Thus, when the Prt+/Prt− lactic bacteria ratio decreases to the point that growth of the Prt− lactic bacteria is significantly inhibited, lactic acid production is also inhibited, and it becomes necessary to reisolate the Prt+ lactic bacteria to restore the acid production rate.

Other disadvantages of cheesemaking operations employing Prt+ lactic bacteria culture systems stem from the fact that significant growth of the Prt+ lactic bacteria in these systems is encouraged and carried out in the cheesemaking vessel and that the growth of such Prt+ lactic bacteria is relatively rapid. For example, careful control over the production of acid by the propagating Prt+ lactic bacteria in the cheesemaking vessel is made difficult because of the relatively rapid rate at which the Prt+ lactic bacteria in the cheesemaking vessel reproduce. Moreover, since the critical production of acid is largely dependent on the substantial initial growth of the Prt+ lactic bacteria in the cheesemaking vessel, conditions within the cheesemaking vessel must be carefully controlled so as to promote initial growth of the Prt+ lactic bacteria and carefully control the growth of the Prt+ lactic bacteria thereafter. Thus, the temperature in, for example, a Cheddar cheesemaking vessel must be raised gradually from 31° C. to 38° C. to optimize initial growth of the Prt+ lactic bacteria and to control the later growth thereof. Such a gradual temperature rise results in a relatively slow production of cheese; the required period of time for making Cheddar cheese using Prt+ lactic bacteria is typically from about three to about five hours from culture addition to salting of the curd.

The relatively long periods of time required to make cheese using Prt+ lactic bacteria and the substantial growth of the Prt+ lactic bacteria accomplished in the cheesemaking vessel result in perhaps the most significant problem associated with the use of Prt+ bacteria—the occurrence and growth of a significant number of bacteriophage in the milk within the cheesemaking vessel. These bacterial viruses are introduced into the cheesemaking operation when lactic bacteria infected with such viruses are present in the bulk culture inoculant or the surrounding cheesemaking environment. Since bacteriophage are reproduced in growing bacteria cells, the growth of bacteriophage is directly dependant upon the growth of the host bacteria. Bacteriophage growth is further enhanced by the presence of calcium ions in the surrounding environment. The prior art has attempted to protect against bacteriophage growth in the bulk culture tank rather than in the cheesemaking vessel, on the theory that lower concentrations of bacteriophage in the bulk culture inoculant would correspondingly reduce the number of bacteriophage in the milk within the cheesemaking vessel.

Generally speaking, bacteriophage populations of $10^7$ to $10^8$ or more bacteriophage plaque forming units per milliliter (pfu/ml) in the resulting whey at the end of the cheesemaking process indicate that there is enough bacteriophage in the cheesemaking operation to render the lactic bacteria culture substantially less effective, if not ineffective. Thus, such bacteriophage populations are considered unacceptable. Unfortunately, this critical limit is often approached or exceeded in the prior art processes using Prt+ lactic bacteria since there is relatively rapid growth of Prt+ lactic bacteria, and thus of bacteriophage, within the cheesemaking vessel.

Moreover, the large number of bacteriophage present in the resulting whey within the cheesemaking vessel has discouraged those skilled in the art from recycling the whey for use in the bulk culture tank in the preparation of other lactic bacteria bulk culture systems. Thus, the problems of bacteriophage in both the bulk culture tank and the cheesemaking vessel have plagued the cheese industry since its incipiency.

From the foregoing, it will be appreciated that what is needed in the art is a method for preparing a lactic bacteria bulk culture and a method for making fermented dairy products (such as cheese) wherein bacteriophage problems are effectively eliminated. Moreover, it would be a significant advancement in the art to provide a method for preparing a lactic bacteria bulk culture and a method for making fermented dairy products wherein bitter flavors are eliminated from the resulting fermented dairy product. Also, it would be a significant advancement in the art to provide a method for preparing a lactic bacteria bulk culture and a method for making fermented dairy products wherein a greater amount of the casein and other proteins in the milk are preserved and transferred to the resultant fermented dairy product. It would be a further advancement in the art to provide a method for preparing a lactic bacteria bulk culture and a method for making fermented dairy products wherein a single phenotype of lactic bacteria is involved, thereby eliminating complex variables in the selection and propagation of bacterial strains. Additionally, it would be a significant advancement in the art to provide a process for making fermented dairy products such as cheese wherein the production of acid is not dependent upon the growth of the lactic bacteria in the cheesemaking vessel, enabling the production of acid to be more carefully controlled. Finally, it would be a significant advancement in the art to provide a process for making fermented dairy products such as cheese wherein the initial temperature in the cheesemaking vessel may be raised higher than those initial temperatures presently experienced in the prior art processes, thereby reducing the required period of time for making the cheese and thereby inhibiting the growth of bacteriophage. Such novel methods are disclosed and claimed herein.

BRIEF SUMMARY AND OBJECTS OF THE INVENTION

The present invention relates to novel methods and media for preparing bulk cultures of proteinase negative lactic bacteria and to novel methods for making fermented dairy products using such proteinase negative lactic bacteria. The invention includes preparing a lactic bacteria bulk culture containing a relatively large number of Prt− lactic bacteria by first preparing a medium suitable for growing Prt− lactic bacteria, such that the medium contains the available nitrogenous nutrients necessary for the growth of the Prt− lactic bacteria. The medium is then introduced into a bulk culture tank, and heated to a temperature sufficient to kill bacteriophage present in the medium. The medium is subsequently cooled to a temperature favorable to the growth of Prt− lactic bacteria and a Prt− lactic bacteria starter is introduced into the medium. The Prt− lactic bacteria are then allowed to propagate to a population sufficient to serve as an inoculant, for example, in making cheese and sufficient to produce the necessary quantities of lactic acid upon introduction into the cheesemaking vessel without substantial further growth of the Prt− lactic bacteria therein.

After preparation of the Prt− lactic bacteria bulk culture, the culture is introduced into a cheesemaking vessel containing a quantity of milk to which is also added a cheesemaking enzyme, for example, rennin. Since the amount of available nitrogenous material in the milk (which is needed to promote growth of the Prt− lactic bacteria) is extremely limited, the further growth of the Prt− lactic bacteria is substantially inhibited after introduction of the Prt− lactic bacteria culture into the cheesemaking vessel. However, the relatively large numbers of Prt− lactic bacteria introduced into the cheesemaking vessel continue to thrive and are already in sufficient number to produce the quantity of lactic acid necessary for making cheese. Concurrently, the enzyme acts upon the milk to produce a cheese curd and whey; when the cheese curd reaches the desired state of development, the whey is removed from the cheesemaking vessel.

Since, contrary to what is done in the prior art processes using Prt+ lactic bacteria, the principal growth of the Prt− lactic bacteria is carried out while preparing the Prt− lactic bacteria bulk culture in the bulk culture tank and substantially limited growth of the Prt− lactic bacteria occurs in the cheesemaking vessel, bacteriophage growth in the cheesemaking vessel is significantly inhibited and bacteriophage problems are effectively eliminated. Consequently, in the present invention, higher levels of bacteriophage can be initially present in the milk within the cheesemaking vessel upon inoculation thereof than can be tolerated in the prior art processes using Prt+ lactic bacteria. This is because the further growth of the bacteriophage within the cheesemaking vessel is substantially inhibited by the restricted further growth of the Prt− lactic bacteria in the cheesemaking vessel.

Moreover, the whey produced according to the novel cheesemaking methods of the present invention may be recycled and used in the preparation of the bulk cultures of Prt− lactic bacteria. Since the Prt− lactic bacteria employed in the novel methods of the present invention do not have a proteinase enzyme system to break up casein in the milk, the bitter flavors associated with such a proteinase enzyme system are reduced, if not eliminated. Moreover, a greater amount of the casein originally present in the milk is preserved and transferred to the resultant cheese. (This is especially important in making fermented products such as cheese and cream cheese where the whey is separated from the curds, a smaller amount of broken down, solubilized protein escaping in the whey than experienced in the prior art.) Additionally, since Prt− lactic bacteria can only reproduce to provide other Prt− lactic bacteria and cannot reproduce to provide their Prt+ phenotypic counterparts, an effectively pure strain of Prt− variants of lactic bacteria can be continuously propagated, thereby eliminating complex variables in the selection and propagation of such Prt− lactic bacteria strains.

The novel methods of the present invention also provide a cheesemaking process in which the production of acid within the cheesemaking vessel can be more carefully controlled, since growth of the Prt− lactic bacteria is accomplished primarily before the Prt− lactic bacteria are introduced into the cheesemaking vessel. Thus, the amount of grown Prt− lactic bacteria introduced into the cheesemaking vessel is controlled, thereby producing a predictable amount of acid in the cheesemaking vessel.

Finally, further growth of the Prt− lactic bacteria in the cheesemaking vessel is relatively insignificant and for the most part unnecessary. Therefore, the temperature in the cheesemaking vessel may be initially raised higher than those initial temperatures presently utilized by prior art processes which require careful control of the temperature within the cheesemaking vessel to promote initial growth of the Prt+ bacteria and to control growth thereafter. Consequently, the required period of time for making cheese using the novel methods of the present invention is substantially reduced in comparison to the prior art processes.

It is, therefore, an object of the present invention to provide methods for preparing a lactic bacteria culture comprising Prt− lactic bacteria for use as an inoculant in making fermented dairy products such as cheese and to provide methods for making fermented dairy products such as cheese using Prt− lactic bacteria.

Another object of the present invention is to provide media suitable for growing Prt− lactic bacteria.

Still another object of the present invention is to provide methods for preparing lactic bacteria bulk cultures and for making fermented dairy products wherein bacteriophage problems are effectively eliminated.

Yet another object of the present invention is to provide methods for preparing lactic bacteria bulk cultures and for making fermented dairy products wherein bitter flavors are substantially reduced or eliminated from the resulting cheese.

A further object of the present invention is to provide methods for making fermented dairy products wherein a greater amount of the casein in the milk is preserved and transferred to the resultant fermented dairy product than is characteristic of the prior art processes.

Another object of the present invention is to provide methods for preparing lactic bacteria bulk cultures and for making fermented dairy products wherein a single phenotype of lactic bacteria is involved, thereby eliminating complex variables in the selection and propagation of bacterial strains.

A still further object of the present invention is to provide methods for making fermented dairy products, such as cheese, wherein the production of acid in the cheesemaking vessel can be carefully controlled and is not dependent upon growth of the lactic bacteria in the cheesemaking vessel.

Yet another object of the present invention is to provide methods for preparing lactic bacteria bulk cultures and for making fermented dairy products, such as cheese, wherein most of the growth of the lactic bacteria is accomplished during preparation of the lactic bacteria bulk culture, before introduction of the culture into the cheesemaking vessel.

A further object of the present invention is to provide methods for making fermented dairy products, such as cheese, wherein the initial temperature in the cheesemaking vessel may be raised higher than those initial temperatures presently experienced in the prior art processes, thereby reducing the required period of time for making the cheese and thereby inhibiting the growth of bacteriophage.

These and other objects and features of the present invention will become more fully apparent from the following description and appended claims, taken in conjunction with the accompanying drawings.

DETAILED DESCRIPTION OF THE PREFERRED EMBODIMENTS

Figure 1:
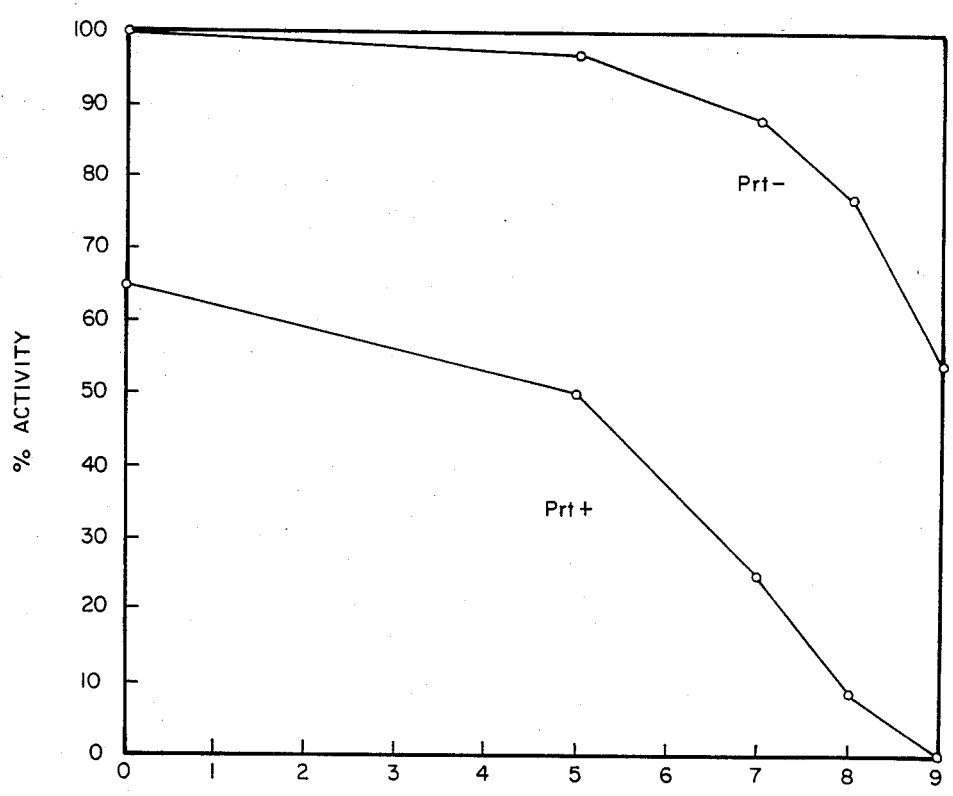
FIG. 1 is a plot of the percent activity of certain Prt+ and Prt− lactic bacteria cultures versus varying concentrations of bacteriophage.

The present invention is directed to the use of proteinase negative lactic bacteria in a process for making fermented dairy products such as Cheddar and other cheeses, cottage cheese, cream cheese, buttermilk, and sour cream. As mentioned above, while the following description is given primarily in terms of a cheesemaking process, this description is equally applicable to the processes for making the other fermented dairy products in accordance with the methods of the present invention, unless otherwise indicated.

It is well-known that Prt− lactic bacteria cannot grow significantly in unaltered whey or milk, since these substrates do not contain the amounts of available nitrogenous nutrients needed for the growth of Prt− lactic bacteria. Thus, Prt+ lactic bacteria have been used in the prior art processes, since (1) Prt− lactic bacteria cannot grow sufficiently in the culture media of the prior art to serve as an effective cheesemaking inoculant and (2) Prt− lactic bacteria cannot grow sufficiently in the milk environment of the cheesemaking vessel to fulfill the prior art requirements of growth therein.

Indeed, the prior art cheesemaking processes have sought to minimize the amount of Prt− lactic bacteria involved because such Prt− lactic bacteria were thought to render the entire lactic bacteria culture too slow in producing acid in the cheesemaking vessel, and therefore unsuitable for purposes of the prior art. Thus, when the concentration of Prt− lactic bacteria in the lactic bacteria cultures reach a certain level in the prior art processes, the cultures are discarded or fresh Prt+ lactic bacteria cultures are isolated.

According to the methods and media of the present invention, however, Prt− lactic bacteria may be used exclusively in the cheesemaking process. Instead of encouraging further growth of the lactic bacteria bulk culture in the cheesemaking vessel, substantially all of the lactic bacteria needed to make the cheese are initially prepared in the bulk culture tank. Thus, to provide the necessary lactic bacteria in the cheesemaking methods of the present invention, lactic bacteria bulk cultures of the present invention contain three to seven times more bacteria cells than those used in the prior art to inoculate the milk, depending upon the acid-producing rates of the lactic bacteria strain involved. In such an augmented Prt− lactic bacteria bulk culture or inoculant, the inoculant contains enough lactic bacteria to aid the rennin enzyme in making cheese without further growth of the Prt− lactic bacteria within the cheesemaking vessel.

Advantageously, the use of Prt− lactic bacteria to prepare a lactic bacteria bulk culture containing substantially all of the lactic bacteria necessary for the cheesemaking process does not have the undesirable results of bitter flavors and lower protein content in the cheese; however, such undesirable results would be experienced if Prt+ lactic bacteria bulk cultures of that magnitude were used, due to the multiplied effects of the external proteinase system of the Prt+ lactic bacteria in such an augmented bulk culture.

Additionally, the bulk culture of the present invention can be comprised exclusively of Prt− lactic bacteria by adding sufficient nitrogenous nutrients to the bulk culture medium to foster such growth. Thus, in contradistinction to the prior art processes, the present invention represents a novel method of propagating lactic bacteria in that the lactic bacteria are grown primarily in the bulk culture tank such that substantial further growth of the lactic bacteria in the cheesemaking vessel is neither necessary nor desirable.

Upon inoculation with these relatively large quantities of Prt− lactic bacteria in the present invention, unexpected results are obtained. For example, bacteriophage problems and bitter flavors are effectively eliminated, the production of lactic acid within the cheesemaking vessel can be more carefully controlled, and cheese can be made even where antibiotics are present in the milk.

Preferred embodiments of the methods and media of the present invention for preparing a bulk culture of Prt− lactic bacteria and of the methods for making fermentable dairy products such as cheese using Prt− lactic bacteria are discussed below.

A medium suitable for growing Prt− lactic bacteria is first prepared. The important characteristics of such a medium is the presence of an energy source (such as lactose or glucose) and the presence of sufficient growth-promoting nitrogenous nutrients (such as yeast autolyzate, protein hydrolyzates, etc.). Lactose and glucose provide metabolic energy to sustain lactic bacteria, while nitrogenous nutrients provide the necessary building blocks for the synthesis of proteins during replication of the lactic bacteria. Since Prt− lactic bacteria do not reproduce adequately in a milk-only or whey-only substrate to serve as an inoculant, nitrogenous nutrients must be added to the milk or whey to enable the Prt− lactic bacteria to grow properly. A whey-based medium is presently preferred since whey is abundantly produced in the cheesemaking process, thereby providing an inexpensive medium base. Moreover, whey has the additional advantage that it also contains a substantial amount of lactose.

One presently preferred embodiment of a medium suitable for growing Prt− lactic bacteria having a whey-based medium is prepared as follows: The medium is prepared by mixing phosphate (for example. in the form of sodium, monoammonium, or diammonium phosphate) or citrate (for example, in the form of sodium citrate) in a concentration of about 0.5% to about 1.5% by weight, yeast autolyzate in a concentration of about 0.3% to about 2.0% by weight, and casein hydrolyzate in a concentration of about 0.1% to about 0.4% by weight, into a whey base. The whey may be obtained from any convenient source, but as discussed in more detail hereinafter, the whey may be fresh liquid whey obtained directly from the cheesemaking methods of the present invention. Additionally, other nitrogenous substrates may be added to the whey, such as additional protein hydrolyzates (e.g., corn steep liquor, hydrolyzed whey proteins, pancreas extract, etc.), to provide additional nutrients for the Prt− lactic bacteria.

Upon the addition of available nitrogenous nutrients needed to render the whey suitable for growing Prt− lactic bacteria (e.g., yeast autolyzate and/or protein hydrolyzates), this whey-based medium provides an inexpensive medium for growing Prt− lactic bacteria. The total concentration of nitrogenous nutrients added to the whey is generally between about 0.3% and about 2% by weight, with the presently preferred range being from about 0.4% to about 1.2% by weight.

EXAMPLE 1

A medium suitable for the growing of Prt− lactic bacteria within the scope of the present invention was prepared by adding yeast autolyzate and casein hydrolyzate to whey obtained from a cheesemaking operation such that the yeast autolyzate was in a concentration of about 0.6% by weight and the casein hydrolyzate was in a concentration of about 0.2% by weight. Enough sodium monophosphate and sodium diphosphate was added such that there was a concentration of about 0.375% sodium monophosphate and about 0.375% sodium diphosphate by weight.

EXAMPLE 2

Another medium suitable for the growing of Prt− lactic bacteria within the scope of the present invention was prepared according to Example 1, except that enough yeast autolyzate was added to the whey to bring the concentration thereof to about 1.2% by weight and except that no casein hydrolyzate was added to the whey.

It should be noted that the foregoing examples are given by way of example only and that many other media suitable for growing Prt− lactic bacteria are also possible. For example, a water-based medium could be employed in which lactose or glucose, and any of the nitrogenous nutrients discussed herein (e.g. yeast, protein hydrolyzates) are mixed with water. Further, milk-based media could also be employed.

One presently preferred embodiment of the methods of the present invention for preparing a bulk culture of Prt− lactic bacteria for use as an inoculant in making fermentable dairy products such as cheese is as follows. A medium suitable for growing Prt− lactic bacteria is first prepared in a bulk culture tank in the manner discussed hereinabove. The medium is then heated to a temperature sufficient to inactivate bacteriophage present in the medium. Generally, heating the medium within the temperature range of about 80° C. to about 150° C. for a period of about 0.1 to about 50 minutes is sufficient to inactivate substantially all of the bacteriophage present in the medium; the presently preferred conditions for conducting such a sterilizing step are at a temperature of about 90° C. for about 45 minutes.

After the medium has been sterilized, it is cooled to a temperature which is favorable to the growth of Prt− lactic bacteria, that is, a temperature within the range of about 20° C. to about 35° C., with the presently preferred temperature being about 27° C. When the medium has been cooled to within the above-indicated temperature range, a Prt− lactic bacteria starter is introduced into the medium and the Prt− lactic bacteria are allowed to grow.

The starter cultures of Prt− lactic bacteria may comprise Prt− variants of any suitable lactic bacteria, such as *Streptococcus lactis* and *Streptococcus cremoris*. It will be recognized that lactic bacteria other than the aforementioned lactic bacteria are suitable, such lactic bacteria being well-known to those of ordinary skill in the art. Moreover, it will be appreciated that genetically modified lactic bacteria, such as lactic bacteria with enhanced acid producing capabilities, may be used in the methods and media of the present invention.

The Prt− lactic bacteria in the bulk culture tank are allowed to propagate to a population sufficient to serve as an inoculant in making cheese; bacteria population in the range of between about $5 \times 10^9$ cells and about $5 \times 10^{10}$ cells per milliliter are suitable, with the presently preferred range being between about $9 \times 10^9$ and about $2 \times 10^{10}$ cells per milliliter. This population can generally be achieved within about 10 to about 24 hours, depending upon the initial number of cells in the inoculant.

While the Prt− lactic bacteria population is propagating within the bulk culture tank, the pH of the medium is maintained within the range of about 5.5 to about 6.6 by adding an acid-neutralizing agent (e.g., ammonia, ammonium hydroxide, or sodium hydroxide) to the medium when the pH drops below 5.5. The presently preferred pH range for the medium of the present invention is from about 6.0 to about 6.4. Alternatively, insoluble phosphate salts may be used to provide internal pH control of the medium within the bulk culture tank.

Additionally, as discussed above, phosphates or citrates may be added to the medium to act as a bacteriophage inhibitor. In one preferred embodiment, the phosphates are added as a fifty-fifty blend of monophosphate and diphosphate sodium or ammonium salts. Alternatively, insoluble phosphates may be added as bacteriophage inhibitors. When coupled with the pH controlled medium discussed herein, it has been found that considerably less phosphate bacteriophage inhibitor is needed to control the bacteriophage within the bulk culture tank than is required by the prior art processes. This is because less calcium is in the form of free calcium ions in the pH controlled medium of the present invention than in the prior art media. For example, where phosphate is used as a bacteriophage inhibitor in preparing the Prt− lactic bacteria culture of the present invention, enough phosphate is added to bring the phosphate concentration of the medium within the range of about 0.5% to about 1.5% by weight, as opposed to the prior art concentrations of about 1.6% to about 3% by weight.

In contradistinction to the prior art processes, the primary growth of the Prt— lactic bacteria is accomplished in the bulk culture tank with relatively little further growth occurring after the Prt— lactic bacteria are introduced into the cheesemaking vessel. Because of this restricted growth of the Prt— lactic bacteria in the cheesemaking vessel, substantially larger amounts of inoculant (e.g., typically about three to seven times the amount of lactic bacteria cells used in the prior art processes employing Prt+ lactic bacteria) are needed to prepare the Prt— lactic bacteria culture for use as an inoculant in the methods of the present invention.

Generally, enough Prt— lactic bacteria inoculant is prepared such that the inoculant represents from about 1% to about 4% of the total volume of milk to be inoculated; the presently preferred range is from about 1.2% to about 2.2%. More importantly, the Prt— lactic bacteria inoculant of the present invention represents from about $1 \times 10^{7.5}$ to about $1 \times 10^9$ total cells per milliliter of milk to be inoculated, with the presently preferred range being from about $1 \times 10^8$ to about $1 \times 10^{8.6}$ total cells per milliliter of milk. This is in contradistinction to the prior art processes employing Prt+ lactic bacteria wherein from about $1 \times 10^7$ to $2 \times 10^7$ cells per milliliter of milk are used to inoculate.

It should be recognized that the above-described ranges for the number of Prt— lactic bacteria cells used in the inoculant of the methods of the present invention could be lowered by the use of genetically modified lactic bacteria which have enhanced lactic acid-producing capabilities.

In one presently preferred embodiment of the methods of the present invention for making fermented dairy products using exclusively Prt— lactic bacteria, a bulk culture of Prt— lactic bacteria of sufficient population to serve as an inoculant for making cheese is prepared as discussed hereinabove. The Prt— lactic bacteria culture is then introduced into a cheesemaking vessel or vat containing a quantity of milk to be made into cheese. A cheesemaking enzyme, such as rennin, is added to the milk in the cheesemaking vessel, and the enzyme begins to act on the milk to produce cheese curds and whey.

Since there is insufficient nitrogenous material to sustain much growth of the Prt— lactic bacteria in the milk environment of the cheesemaking vessel, the further growth of the Prt— lactic bacteria within the cheesemaking vessel is substantially inhibited. Generally, the growth of the Prt— lactic bacteria within the cheesemaking vessel has been found to be only from about 0% to about 25% of the total cell mass originally in the bulk culture inoculant upon introduction of the inoculant into the cheesemaking vessel. The exact amount of further growth of the Prt— lactic bacteria within the cheesemaking vessel depends upon such factors as the temperature within the cheesemaking vessel, the amount of nitrogenous nutrients left in the bulk culture inoculant upon introduction of the inoculant into the cheesemaking vessel, and the particular strain of Prt— lactic bacteria employed.

Such restricted growth of the Prt— lactic bacteria within the cheesemaking vessel represents only about 10-20% of the growth which is experienced with Prt+ lactic bacteria in the prior art processes. Although the further growth of the Prt— lactic bacteria in the cheesemaking vessel is substantially inhibited, the relatively larger Prt— lactic bacteria bulk culture used to inoculate the milk provides adequate Prt— bacteria to produce the necessary lactic acid needed to aid the rennin in accomplishing coagulation of the milk and syneresis of the curd. Such inhibition of bacteria growth results in a corresponding inhibition of bacteriophage growth and allows the production of lactic acid within the cheesemaking vessel to be carefully controlled and predicted. This is true even where some antibiotics are present in the milk.

Moreover, by eliminating the need to further propagate the Prt— lactic bacteria in the cheesemaking vessel, the temperature within the cheesemaking vessel may be raised more rapidly than in the prior art processes in which the temperature must be carefully controlled to accommodate growth of the Prt+ lactic bacteria. For example, in the cheesemaking methods of the present invention, temperatures within the range of about 32° C. to about 42° C. can be employed initially, whereas the prior art processes generally start at a temperature of about 31° C. and do not reach a temperature of 38° C. until about 1.5 hours into the cheesemaking process. The presently preferred temperature range for the temperature within the cheesemaking vessel throughout the cheesemaking process in the methods of the present invention is about 36° C. to about 40° C., with the most presently preferred temperature range being from about 38° C. to about 40° C. By maintaining a temperature of about 38°-40° C. within the cheesemaking vessel throughout the entire cheesemaking process in this embodiment of the present invention, the cheese is produced within a period of about 2.5 hours to about 4 hours (from culture addition to salting of the curd), as opposed to the three-five hour period required in the prior art processes.

When the cheese curd reaches the desired stage of development, the whey is removed from the cheesemaking vessel and the cheese curd is salted and pressed by methods well-known in the art. Of particular significance is the fact that since the growth of the Prt— lactic bacteria within the cheesemaking vessel is relatively small, the corresponding growth of bacteriophage within the cheesemaking vessel is also significantly reduced. This is because nonreplicating Prt— lactic bacteria cells do not produce bacteriophage.

Indeed, because of the substantially inhibited growth of bacteriophage within the cheesemaking vessel in the methods of the present invention, it has been found that the bacteriophage populations that are tolerable in the Prt— lactic bacteria culture of the present invention used to inoculate the milk are substantially higher ($10^3$ to $10^6$ pfu/ml) than those bacteriophage populations which are tolerable in the Prt+ lactic bacteria cultures used as inoculants in the processes of the prior art ($10^{-3}$ to $10^0$ pfu/ml). Even after inoculation with bacteria cultures having $10^3$ to $10^6$ bacteriophage pfu/ml, the critical bacteriophage population of $10^7$ pfu/ml is not reached within the cheesemaking vessel in the present invention, due to such inhibited growth of the bacteriophage. Consequently, concerns of bacteriophage contamination of the milk by the lactic bacteria culture used to inoculate the milk are significantly reduced, if not effectively eliminated in the cheesemaking methods of the present invention wherein Prt— lactic bacteria are employed.

Another advantage stemming from the fact that growth of the Prt— lactic bacteria is substantially inhibited within the cheesemaking vessel is that such limited growth restricts the ability of antibiotics to act on the lactic bacteria within the cheesemaking vessel and to render the bacteria culture ineffective to produce cheese. Thus, where the milk to be made into cheese contains a significant amount of antibiotics, due, for example, to the treatment of mastitis of the cows providing the milk, the cheesemaking method of the present invention using Prt− lactic bacteria can be used to make cheese out of the milk containing significant quantities of antibiotics, whereas prior art processes would be unable to do so. Although the quantities of antibiotics in this cheese may exceed the acceptable limit for human consumption, such cheese could be used as animal feed.

As discussed hereinabove, the retarded growth of bacteriophage within the cheesemaking vessel in the methods of the present invention allows for the introduction of much greater initial populations of bacteriophage into the cheesemaking vessel (by way of the bulk culture inoculant) than do the prior art processes. Moreover, it has been found that, surprisingly, Prt− lactic bacteria cultures retain their activity in dramatically larger concentrations of bacteriophage than do Prt+ lactic bacteria. This surprising, yet extremely valuable characteristic of Prt− lactic bacteria is illustrated in FIG. 1. The experimental procedure for which the results are reported in FIG. 1 was conducted as follows.

Various Prt+ and Prt− lactic bacteria cultures of UL7 (Utah lactic 7), UL8, UL21, UL33, UC91 (Utah cremoris 91), and UC171 were first prepared and isolated. The Prt+ lactic bacteria cultures were propagated in sterile reconstituted nonfat dry milk and the Prt− lactic bacteria cultures were propagated in a sterile reconstituted nonfat dry milk substrate containing 0.5% yeast extract by weight. About 0.2 milliliters of each culture was placed in 10 milliliters of milk, and 0.225 milliliter aliquots of each mixture were placed in successive wells along a Microtiter plate. ("Microtiter" is a registered trademark owned by Dynatek Laboratories, Inc.) An 0.25 milliliter aliquot of a $1 \times 10^9$ pfu/ml homologous bacteriophage stock solution was placed at the first position on the Microtiter plate and dilutions of the bacteriophage concentration were accomplished at successive positions on the microtiter plate by a manual diluter apparatus, each successive position on the microtiter plate having 1/10 the bacteriophage concentration of the previous position. The Microtiter plate and culture samples were then incubated at about 38° C. for about five hours. The pH was measured and the activity of each culture was then determined by calculating the acid produced by each culture in the presence of the bacteriophage. The results of the experiments for the Prt+ and Prt− forms of each of the six bacteria strains were averaged; the results are reported in FIG. 1.

As seen in FIG. 1, the Prt− lactic bacteria cultures within the cheesemaking vessel were still 97% active in the presence of $10^5$ bacteriophage pfu/ml in comparison with about 50% activity for the Prt+ lactic bacteria cultures. Such phenomenal activity of Prt− lactic bacteria in the presence of relatively large amounts of bacteriophage allows cheesemaking to occur in the presence of much more bacteriophage using the present invention than is possible in the prior art.

Another advantage of using the Prt− lactic bacteria in the methods of the present invention is the surprising ability of the Prt− lactic bacteria cultures prepared in the bulk culture tank to survive repeated bacteriophage attacks. When prepared in accordance with the present invention, Prt− lactic bacteria cultures with a population of $1 \times 10^{10}$ cells per milliliter or more remain active for days. Experiments showing the comparative ability of Prt+ versus Prt− lactic bacteria cultures to survive repeated bacteriophage attack were run using the well-known Heap-Lawrence technique; the results of these experiments are reported in FIG. 2.

Figure 2:
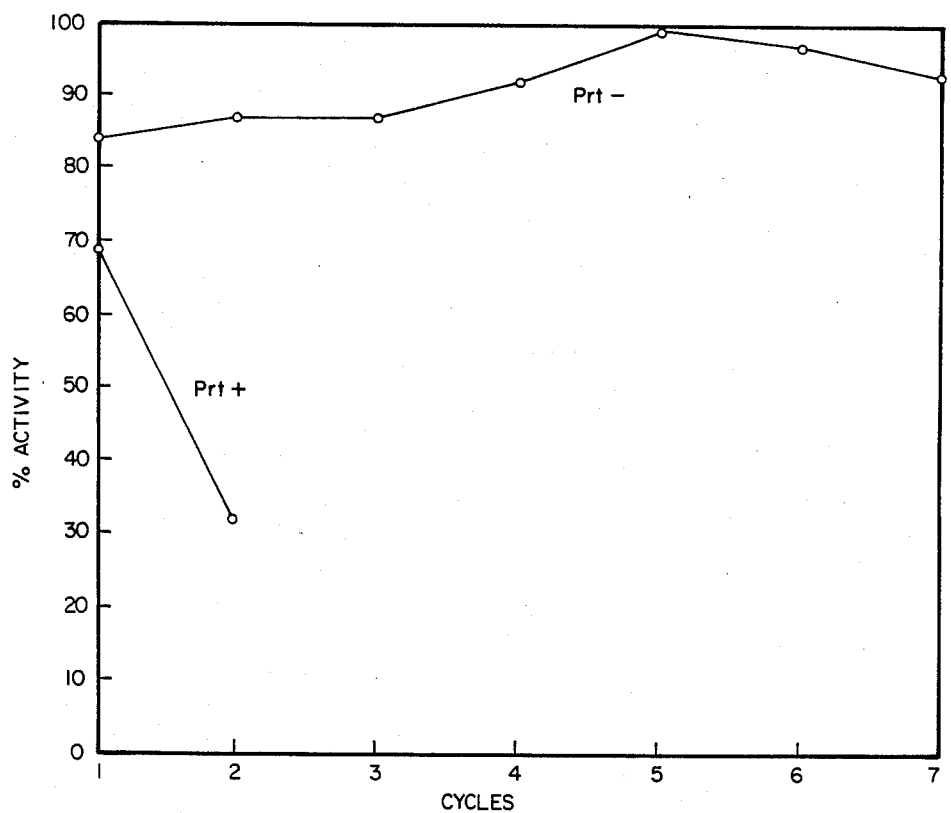
FIG. 2 is a plot of the percent activity of certain Prt+ and Prt− lactic bacteria cultures versus the number of cheesemaking cycles through which the whey used to grow the lactic bacteria cultures had passed.

In the experiments reported in FIG 2, various Prt+ and Prt− lactic bacteria cultures of UL8 (Utah lactic 8), UL21, and UC171 (Utah cremoris 171) were first prepared and isolated. The Prt+ lactic bacteria cultures were propagated in sterile reconstituted nonfat dry milk and the Prt− lactic bacteria cultures were propagated in the same sterile reconstituted nonfat dry milk substrate except that 0.5% dry yeast extract by weight was added to the substrate. About 0.2 milliliters of each culture, 0.1 milliliters of whey obtained from a cheesemaking operation, and 0.1 milliliters of a composite bacteriophage stock solution containing several bacteriophage homologs were placed into 10 milliliters of milk and incubated at about 38° C. for about five hours. After incubation, the pH was measured and the activity of each culture was determined by calculating the acid which was produced during incubation. The whey was then filtered from this first simulated cheesemaking cycle and used to prepare another lactic bacteria culture following the same procedure outlined above (with the exception, of course, that the whey used was the recycled whey from the previous experiment). These simulated cheesemaking cycles or experiments were repeated recycling the whey produced in one experiment into the successive experiment, thus allowing the initially low numbers of bacteriophage in the experiments to reach significantly higher numbers. The pH change corresponding to the activity of the cultures in each cycle was determined by titration and the results of these experiments for the Prt+ and Prt− forms of each of the three bacteria strains were averaged; the results are reported in FIG. 2.

As seen in FIG. 2, after two cycles the Prt+ lactic bacteria cultures had about 30% activity, while the Prt− lactic bacteria cultures maintained about 85–99% activity through seven cycles. The results reported in FIG. 2 dramatically illustrate the superiority of the Prt− lactic bacteria cultures over the Prt+ lactic bacteria cultures in surviving repeated bacteriophage attack.

It is noteworthy that the whey produced using the cheesemaking methods of the present invention may be recycled to the bulk culture tank for use in the preparation of other Prt− lactic bacteria cultures. Recycling the whey in this fashion yields a much more economical medium than the relatively expensive milk-based media used to prepare the Prt+ lactic bacteria cultures of the prior art.

It is also noteworthy that the internal peptidases and internal proteinases responsible for aging and ripening of the cheese are also present in the Prt− lactic bacteria, and thus aging and ripening of the cheese are not affected by the use of Prt− lactic bacteria. Indeed, the external proteinase enzyme system which is absent in the Prt− lactic bacteria is not needed for aging and ripening. Thus, the internal proteinases which are found in Prt−, as well as in Prt+ lactic bacteria, enable the methods of the present invention employing Prt− lactic bacteria to be used without affecting the aging process.

It should be recognized that, although the above-described methods and media for preparing a lactic bacteria culture and the above-described methods for making fermentable dairy products such as cheese include the use of exclusively Prt− lactic bacteria, it should be recognized that the presence of a relatively small proportion of Prt+ lactic bacteria in the Prt− lactic bacteria culture of the present invention will not destroy the favorable advantages of an exclusive Prt− lactic bacteria system. Therefore, it will be recognized, that a system consisting of primarily Prt− lactic bacteria, but containing a relatively small amount of Prt+ lactic bacteria, is within the scope of the methods and media of the present invention. However, if the concentration of Prt+ lactic bacteria becomes great enough, the advantages of a Prt− lactic bacteria system as described herein will begin to disappear. Thus, it will be recognized that in the Prt− lactic bacteria system of the present invention, it is desirable to avoid concentrations of Prt+ lactic bacteria that would destroy the advantages achieved by the use of Prt− lactic bacteria.

EXAMPLE 3

An example of a cheesemaking method within the scope of the present invention is described below. Cultures of *Streptococcus lactis* and *Streptococcus cremoris* lactic bacteria cultures were propagated, and the Prt− lactic bacteria were isolated and used in the preparation of the Prt− lactic bacteria culture of this example. A medium suitable for growing the Prt− lactic bacteria was prepared by blending 4.5% by weight of dried sweet whey and 0.5% by weight of yeast extract into 95% by weight of water, thereby producing a 5% whey solids-yeast medium. Sufficient dried sweet whey, yeast extract, and water were mixed in these proportions to produce about 46 gallons of medium. The medium was then autoclaved at 121° C. for fifteen minutes and then cooled to about 27° C. The Prt− lactic bacteria were introduced into the whey-based medium and allowed to propagate for about 14 hours to a population of about $1 \times 10^{10}$ cells per milliliter, while constantly stirring the medium and maintaining the pH of the medium within the range of about 6.0 to about 6.4 by adding ammonium hydroxide to raise the pH when it reached 6.0. The resultant Prt− lactic bacteria culture and about 210 grams of a rennin enzyme were introduced into a cheesemaking vessel containing 2300 gallons of milk. The temperature of the milk within the cheesemaking vessel was raised gradually from about 31° C. to about 38° C. for a period of about 2.5 hours after which the produced whey was separated from the cheese curd. (It should be noted that, although temperatures of 31° C.–38° C. were used for purposes of this experiment, in the present invention, the presently preferred temperature range for the temperature within the cheesemaking vessel is about 36° C.–40° C., with the presently most preferred temperature range being about 38° C.–40° C.). The resultant cheese was not bitter, and the resultant whey had a bacteriophage population of about $10^0$ pfu/ml.

Experimental studies of the lactic acid producing rates of various Prt+ and Prt− lactic bacteria were run at various temperatures, e.g., 36°, 38°, 40°, 42° and 44° C. Prt+ and Prt− lactic bacteria cultures of UC171 (Utah cremoris 171) were first prepared and isolated. The Prt+ lactic bacteria cultures were propagated in a sterile reconstituted nonfat dry milk substrate and the Prt− lactic bacteria cultures were propagated in the same substrate to which was added 0.5% dry yeast extract by weight. The propagated cultures were then added to milk in sufficient quantities to produce a 2% Prt+ lactic bacteria inoculant and an 8% Prt− lactic bacteria inoculant. The cultures were then incubated at the various temperatures for about five hours. The make time (from introduction of the culture to salting of the curd) using each of the cultures in a Cheddar cheesemaking process was then estimated, the estimated make time being based on the observed amount of lactic acid produced by each culture. These estimated make times are tabulated in Table I below. At each temperature, lactic acid production was measured for both the Prt− and Prt+ lactic bacteria. These experiments illustrate the exceptional stability in the rate of acid production when using Prt− lactic bacteria in the processes of the present invention.

TABLE I

EFFECTS OF TEMPERATURE ON THE ESTIMATED MAKE TIME OF CHEDDAR CHEESE USING PRT+ VERSUS PRT− LACTIC BACTERIA CULTURES

| Example | Temperature (°C.) | Make Time (Hours) Prt+ | Prt− |
|---|---|---|---|
| 4 | 36 | 1.9 | 3.2 |
| 5 | 38 | 2.5 | 3.3 |
| 6 | 40 | 4.8 | 3.7 |
| 7 | 42 | 13.1 | 6.4 |
| 8 | 44 | 43.0 | 23.2 |

As seen in Table I, the estimated make time (from introduction of the culture to salting of the curd), and thus the acid production rate, was considerably less variable at the various temperatures in the Prt− lactic bacteria system than in the Prt+ lactic bacteria system. Such stability in the acid production rate renders the acid producing capabilities of Prt− lactic bacteria cultures much more predictable. It will be recognized that the estimated make times reported in Table I (as well as Table II below) are for the given culture inoculants. It will therefore be appreciated by those of ordinary skill in the art that by using inoculants containing a larger number of lactic bacteria, these estimated make times would decrease correspondingly.

Other experimental studies of the lactic acid producing rates of various Prt+ and Prt− lactic bacteria were run at various temperatures, e.g., 32°, 34°, 36°, 38°, 40°, 42°, and 44° C. Prt+ and Prt− lactic bacteria cultures of UC 73 (Utah cremoris 73) were first prepared, isolated, propagated, and incubated according to the procedure of the experiments reported in Table I. The make time (from introduction of a cottage cheesemaking culture and enzyme to cutting of the curd) using each of the cultures in a cottage cheesemaking process was then estimated, the estimated make time being based on the observed amount of lactic acid produced by each culture. These estimated make times are reported in Table II below. At each temperature, lactic acid production was measured for both the Prt+ and Prt− lactic bacteria. These experiments illustrate the stability of the acid production rate of Prt− lactic bacteria over a wider range of temperatures in the manufacture of cottage cheese.

TABLE II
EFFECTS OF TEMPERATURE ON THE ESTIMATED MAKE TIME OF COTTAGE CHEESE USING PRT+ VERSUS PRT− LACTIC BACTERIA CULTURES

| Example | Temperature (°C.) | Make Time (Hours) Prt+ | Make Time (Hours) Prt− |
|---------|-------------------|------|------|
| 9  | 32 | 4.0   | 5.1  |
| 10 | 34 | 5.0   | 5.1  |
| 11 | 36 | 7.0   | 5.1  |
| 12 | 38 | 7.9   | 5.5  |
| 13 | 40 | 18.3  | 7.3  |
| 14 | 42 | 42.3  | 9.2  |
| 15 | 44 | 550.0 | 11.7 |

Again, as seen in Table II, the estimated make time (from introduction of the culture and enzyme to cutting of the curd), and thus the acid production rate, was considerably more stable in the Prt− lactic bacteria experiments than in the experiments employing Prt+ lactic bacteria. Thus, these experiments illustrate that the production of lactic acid is more controllable when using Prt− lactic bacteria than when Prt+ lactic bacteria are used.

From the foregoing, it will be appreciated that the methods and media of the present invention provide a viable system for the exclusive use or primary use of Prt− lactic bacteria in making fermented dairy products. Moreover, the methods and media of the present invention provide a process for making fermented dairy products wherein bacteriophage problems are effectively eliminated, bitter flavors in the resulting fermented dairy product or cheese are eliminated, a greater amount of the casein in the milk is preserved and transferred to the resultant fermented dairy product or cheese than is characteristic of the prior art processes, complex variables in the selection and propagation of bacterial strains are eliminated, the production of acid in the cheesemaking vessel is carefully controlled and is not dependent upon the growth of the lactic bacteria in the cheesemaking vessel, most of the growth of the lactic bacteria is accomplished during the preparation of the lactic bacteria bulk culture before introduction of the culture into the cheesemaking vessel with substantially little further growth of the lactic bacteria occurring after introduction of the culture into the cheesemaking vessel, and the initial temperature in the cheesemaking vessel can be raised higher than those initial temperatures presently experienced in the prior art processes so as to reduce the required period of time for making the fermented dairy product.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All claims which come within the meaning and range of equivalency of the claims are to be embraced within their scope.

What is claimed and desired to be secured by United States Letters Patent is:

1. A method for making Cheddar cheese using proteinase negative lactic bacteria, comprising the steps of:
    preparing a culture of proteinase negative lactic bacteria of sufficient population to serve as an inoculant for making Cheddar cheese, said population comprising from about $5 \times 10^9$ to about $5 \times 10^{10}$ cells per milliliter and essentially all of the lactic bacteria in the culture being proteinase negative lactic bacteria, said method being carried out with essentially no addition of proteinase positive lactic bacteria before formation of cheese curd;
    introducing the culture of proteinase negative lactic bacteria and a Cheddar cheese making enzyme into a vessel containing a quantity of milk, further growth of the proteinase negative lactic bacteria being substantially inhibited by introduction of the proteinase negative lactic bacteria culture into the milk within the vessel; and
    allowing the enzyme to act on the milk to produce a Cheddar cheese curd.

2. A method as defined in claim 1 wherein the temperature in the vessel is maintained within the range of about 32° C. to about 42° C.

3. A method as defined in claim 1 wherein the temperature in the vessel is maintained within the range of about 36° to about 40° C.

4. A method as defined in claim 1 wherein the enzyme acts on the milk to produce the cheddar cheese curd and whey and wherein at least a portion of the whey is used to prepare the culture of proteinase negative lactic bacteria.

5. A method as defined in claim 1 wherein the culture preparing step comprises:
    preparing a medium suitable for growing proteinase negative lactic bacteria;
    heating the medium to a temperature sufficient to inactivate bacteriophage present in the medium;
    cooling the medium to a temperature favorable to the growth of proteinase negative lactic bacteria;
    introducing proteinase negative lactic bacteria into the medium; and
    allowing the proteinase negative lactic bacteria to propagate to said population of about $5 \times 10^9$ to about $5 \times 10^{10}$ cells per milliliter.

6. A method as defined in claim 5 wherein said medium comprises whey.

7. A method as defined in claim 6 wherein said whey is obtained directly from a cheesemaking operation without substantial alteration of the chemical content thereof.

8. A method as defined in claim 5 wherein said medium comprises a nitrogenous substrate in a concentration of about 0.3% to about 2.0% by weight.

9. A method as defined in claim 8 wherein said nitrogenous substrate comprises yeast.

10. A method as defined in claim 8 wherein said nitrogenous substrate comprises protein hydrolyzates.

11. A method as defined in claim 5 further comprising the step of adding phosphate to the medium in an amount sufficient to bring the phosphate concentration of the medium within the range of about 0.5% to about 1.5% by weight.

12. A method as defined in claim 5 further comprising the step of maintaining the pH of the medium within the range of about 5.5 to about 6.6 by introducing an acid neutralizing agent into the medium when the pH of the medium drops below 5.5.

13. A method as defined in claim 5 wherein the heating step comprises heating the medium to a temperature within the range of about 80° C. to about 150° C. for a period of about 0.1 to about 50 minutes.

14. A method as defined in claim 5 wherein the cooling step comprises cooling the medium to a temperature within the range of about 20° C. to about 35° C.

15. A method as defined in claim 1 wherein the further growth of the proteinase negative lactic bacteria in the vessel is limited to less than about 25%.

16. A method as defined in claim 1 wherein the milk within the vessel contains antibiotics.

17. A method for making Cheddar cheese using proteinase negative lactic bacteria, comprising the steps of:
preparing a culture of proteinase negative lactic bacteria of sufficient population to serve as an inoculant for making Cheddar cheese, said population comprising from about $5 \times 10^9$ to about $5 \times 10^{10}$ cells per milliliter and essentially all of the lactic bacteria in the culture being proteinase negative lactic bacteria, said method being carried out with essentially no addition of proteinase positive lactic bacteria before formation of cheese curd;
introducing the culture of proteinase negative lactic bacteria and a Cheddar cheese making enzyme into a vat containing a quantity of milk;
maintaining the temperature within the vat within the range of about 36° C. to about 40° C.;
inhibiting further growth of the proteinase negative lactic bacteria in the vat to less than about 25%;
allowing action of the enzyme on the milk in the vat to produce a Cheddar cheese curd and whey;
removing the whey from the vat after the Cheddar cheese curd has developed; and
recycling at least a portion of the whey to the culture preparing step for use in preparing the culture of proteinase negative lactic bacteria.

18. A method as defined in claim 17 wherein the culture preparing step comprises:
placing a quantity of whey into a culture growing vessel;
adding yeast and protein hydrolyzates to the whey in a concentration of about 0.4% to about 1.2% by weight;
adding sufficient phosphate to the whey to bring the phosphate concentration of the whey within the range of about 0.5% to about 1.5% by weight;
heating the whey to a first temperature sufficient to inactivate bacteriophage present in the whey, said first temperature being within the range of about 85° C. to about 95° C. for a period of about 40 minutes to about 50 minutes;
cooling the whey to a second temperature favorable to the growth of proteinase negative lactic bacteria, said second temperature being within the range of about 25° C. to about 30° C.;
introducing proteinase negative lactic bacteria into the whey;
maintaining the pH of the whey within the range of about 6.0 to about 6.4; and
allowing the proteinase negative lactic bacteria in the culture growing vessel to propagate to a population of from about $9 \times 10^9$ to about $2 \times 10^{10}$ cells per milliliter.

19. A method for making cottage cheese using proteinase negative lactic bacteria, comprising the steps of:
preparing a culture of proteinase negative lactic bacteria of sufficient population to serve as an inoculant for making cottage cheese, said population comprising from about $5 \times 10^9$ to about $5 \times 10^{10}$ cells per milliliter and essentially all of the lactic bacteria in the culture being proteinase negative lactic bacteria, said method being carried out with essentially no addition of proteinase positive lactic bacteria before formation of cheese curd;
introducing the culture of proteinase negative lactic bacteria and a cottage cheese making enzyme into a vessel containing a quantity of milk, further growth of the proteinase negative lactic bacteria being substantially inhibited by introduction of the proteinase negative lactic bacteria culture into the milk within the vessel; and
allowing the enzyme to act on the milk to produce a cottage cheese curd.

20. A method as defined in claim 19 wherein the temperature in the vessel is maintained within the range of about 32° C. to about 42° C.

21. A method as defined in claim 19 wherein the enzyme acts on the milk to produce the cottage cheese curd and whey and wherein at least a portion of the whey is used to prepare the culture of proteinase negative lactic bacteria.

22. A method as defined in claim 19 wherein the culture preparing step comprises:
preparing a medium suitable for growing proteinase negative lactic bacteria;
heating the medium to a temperature sufficient to inactivate bacteriophage present in the medium;
cooling the medium to a temperature favorable to the growth of proteinase negative lactic bacteria;
introducing proteinase negative lactic bacteria into the medium; and
allowing the proteinase negative lactic bacteria to propagate to said population of about $5 \times 10^9$ to about $5 \times 10^{10}$ cells per milliliter.

23. A method as defined in claim 22 wherein said medium comprises whey.

24. A method as defined in claim 23 wherein said whey is obtained directly from a cheese making operation without substantial alteration of the chemical content thereof.

25. A method as defined in claim 22 wherein said medium comprises a nitrogenous substrate in a concentration of about 0.3% to about 2.0% by weight.

26. A method as defined in claim 25 wherein said nitrogenous substrate comprises yeast.

27. A method as defined in claim 25 wherein said nitrogenous substrate comprises protein hydrolyzates.

28. A method as defined in claim 22 further comprising the step of adding phosphate to the medium in an amount sufficient to bring the phosphate concentration of the medium within the range of about 0.5% to about 1.5% by weight.

29. A method as defined in claim 22 further comprising the step of maintaining the pH of the medium within the range of about 5.5 to about 6.6 by introducing an acid neutralizing agent into the medium when the pH of the medium drops below 5.5.

30. A method as defined in claim 22 wherein the heating step comprises heating the medium to a temperature within the range of about 80° C. to about 150° C. for a period of about 0.1 to about 50 minutes.

31. A method as defined in claim 22 wherein the cooling step comprises cooling the medium to a temperature within the range of about 20° C. to about 35° C.

32. A method as defined in claim 19 wherein the further growth of the proteinase negative lactic bacteria in the vessel is limited to less than about 25%.

33. A method as defined in claim 19 wherein the milk within the vessel contains antibiotics.

34. A method for making cottage cheese using proteinase negative lactic bacteria, comprising the steps of:

preparing a culture of proteinase negative lactic bacteria of sufficient population to serve as an inoculant for making cottage cheese, said population comprising from about $5 \times 10^9$ to about $5 \times 10^{10}$ cells per milliliter and essentially all of the lactic bacteria in the culture being proteinase negative lactic bacteria, said method being carried out with essentially no addition of proteinase positive lactic bacteria before formation of cheese curd;

introducing the culture of proteinase negative lactic bacteria and a cottage cheese making enzyme into a vat containing a quantity of milk;

maintaining the temperature within the vat within the range of about 32° C. to about 42° C.;

inhibiting further growth of the proteinase negative lactic bacteria in the vat to less than about 25%;

allowing action of the enzyme on the milk in the vat to produce a cottage cheese curd and whey;

removing the whey from the vat after the cottage cheese curd has developed; and recycling at least a portion of the whey to the culture preparing step for use in preparing the culture of proteinase negative lactic bacteria.

35. A method as defined in claim 34 wherein the culture preparing step comprises:

placing a quantity of whey into a culture growing vessel;

adding yeast and protein hydrolyzates to the whey in a concentration of about 0.4% to about 1.2% by weight;

adding sufficient phosphate to the whey to bring the phosphate concentration of the whey within the range of about 0.5% to about 1.5% by weight;

heating the whey to a first temperature sufficient to inactivate bacteriophage present in the whey, said first temperature being within the range of about 85° C. to about 95° C. for a period of about 40 minutes to about 50 minutes;

cooling the whey to a second temperature favorable to the growth of proteinase negative lactic bacteria, said second temperature being within the range of about 25° C. to about 30° C.;

introducing proteinase negative lactic bacteria into the whey;

maintaining the pH of the whey within the range of about 6.0 to about 6.4; and allowing the proteinase negative lactic bacteria in the culture growing vessel to propagate to a population of from about $9 \times 10^9$ to about $2 \times 10^{10}$ cells per milliliter.

* * * * *

UNITED STATES PATENT AND TRADEMARK OFFICE
CERTIFICATE OF CORRECTION

PATENT NO. :   4,554,165

DATED      :   November 19, 1985

INVENTOR(S) :  Gary H. Richardson

It is certified that error appears in the above-identified patent and that said Letters Patent is hereby corrected as shown below:

```
    Column 2, line 27, "introduction of a Prt-" should be
--introduction of a Prt+--
    Column 3, line 27, "nitorgenous" should be --nitrogenous--
    Column 9, line 8, "for example." should be --for example,--
```

Signed and Sealed this

Twenty-fifth Day of March 1986

[SEAL]

Attest:

DONALD J. QUIGG

Attesting Officer

Commissioner of Patents and Trademarks